United States Patent [19]

Takaya et al.

[11] 4,367,228

[45] Jan. 4, 1983

[54] CEPHEM COMPOUND AND COMPOSITION

[75] Inventors: Takao Takaya, Kawanishi; Yoshikazu Inoue, Amagasaki; Masayoshi Murata, Mino; Hisashi Takasugi, Kohamanishi, all of Japan

[73] Assignee: Fujisawa Pharmaceutical Co., Ltd., Osaka, Japan

[21] Appl. No.: 201,913

[22] Filed: Oct. 29, 1980

[51] Int. Cl.³ .................. C07D 501/38; A61K 31/845
[52] U.S. Cl. ........................................ 424/246; 544/25
[58] Field of Search ........................ 544/16, 25, 26, 21, 544/27, 28, 30; 424/246

[56] References Cited

U.S. PATENT DOCUMENTS 4,098,888  7/1978  Ochiai et al. ................. 544/25
4,200,575  4/1980  Numada et al. ............... 544/25
4,278,671  7/1981  Ochiai et al. ................. 544/25

FOREIGN PATENT DOCUMENTS 853545  10/1977  Belgium .
865632  10/1978  Belgium .
54-9296  1/1979  Japan .

Primary Examiner—Nicholas S. Rizzo
Attorney, Agent, or Firm—Oblon, Fisher, Spivak, McClelland & Maier

[57] ABSTRACT

This invention relates to new compounds of high antibiotic activity of the formula:

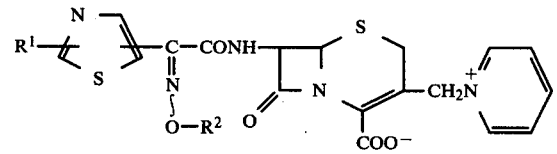

wherein
$R^1$ is amino or a protected amino group; and
$R^2$ is $C_2$ to $C_6$ alkyl.

2 Claims, No Drawings

CEPHEM COMPOUND AND COMPOSITION

The present invention relates to new cephem compounds and pharmaceutically acceptable salts thereof. More particularly, it relates to new cephem compounds and pharmaceutically acceptable salts thereof, which have antimicrobial activities and to processes for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula (I).

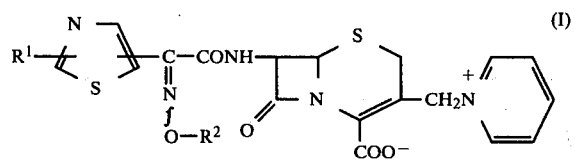

wherein
$R^1$ is amino or a protected amino group; and
$R^2$ is $C_2$ to $C_6$ alkyl.

According to the present invention, the new cephem compounds (I) can be prepared by various processes which are illustrated in the following schemes.

Process 1.

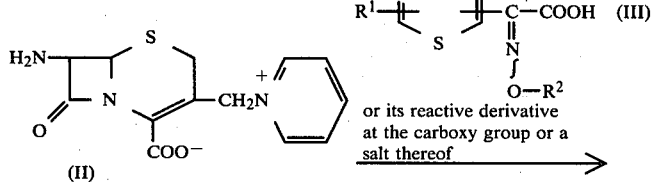

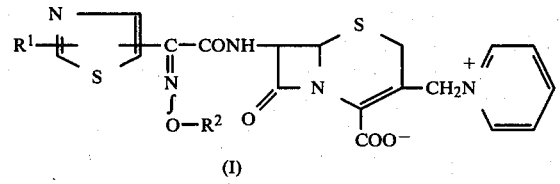

Process 2.

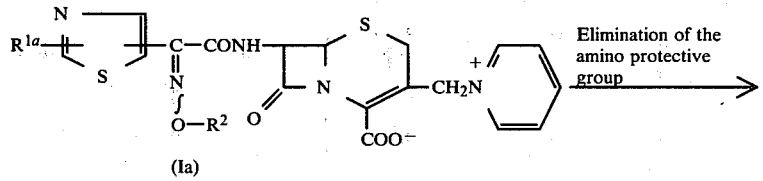

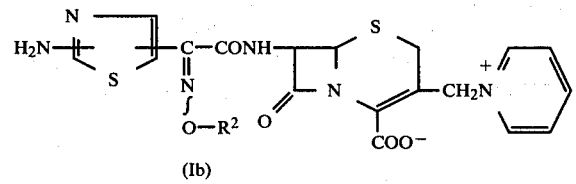

wherein
$R^1$ and $R^2$ are each as defined above, and
$R^{1a}$ is a protected amino group.

Regarding the object compounds (I), (Ia) and (Ib) and the starting compound (III), it is to be understood that they include tautomeric isomers. That is, in case that the group of formula:

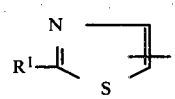

($R^1$ is as defined above) is contained in the molecules of said object and starting compounds, said group of the formula can also be alternatively represented by its tautomeric formula:

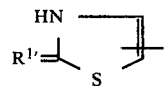

($R^{1'}$ is imino or a protected imino group.) That is, the both of said groups are in the state of equilibrium each other and such tautomerism can be represented by the following equilibrium.

wherein $R^1$ and $R^{1'}$ are each as defined above.

These types of tautomerism between the amino-compound and the corresponding imino-compound as stated above have been well known in the literature, and it is obvious to a person skilled in the arts that both of the tautomeric isomers are easily convertible reciprocally and are included within the same category of the compound per se. Accordingly, the both of the tautomeric forms of the object compounds (I), (Ia) and (Ib) and the starting compound (III) are clearly included within the scope of the present invention. In the present specification and claims, the object and starting compounds including the group of such tautomeric isomers are represented by using one of the expressions therefor, that is the formula:

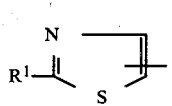

Furthermore, regarding the object compounds (I), (Ia) and (Ib) and the starting compound (III), it is to be understood that said object and starting compounds include syn isomer, anti isomer and a mixture thereof. For example, with regard to the object compound (I), syn isomer means one geometrical isomer having the partial structure represented by the following formula:

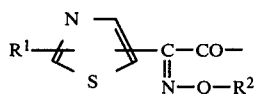

(wherein $R^1$ and $R^2$ are each as defined above) and anti isomer means the other geometrical isomer having the partial structure represented by the following formula:

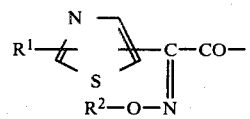

(wherein $R^1$ and $R^2$ are each as defined above).

Regarding the other object and starting compounds as mentioned above, the syn isomer and the anti isomer can also be referred to the same geometrical isomers as illustrated for the compound (I).

Suitable pharmaceutically acceptable salts of the object compounds (I) are conventional non-toxic salt and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, etc.), an inorganic acid salt (e.g. hydrochloride, hydrobromide, sulfate, phosphate, etc.), or a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable "protected amino" for $R^1$ and $R^{1a}$ may include an acylamino or an amino group substituted by a conventional protecting group such as ar(lower)alkyl which may have at least one suitable substituent(s), (e.g. benzyl, trityl, etc.) or the like.

Suitable acyl moiety in the term "acylamino" may include carbamoyl, aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.);

lower alkoxycarbonyl (e.g. methoxycarbonyl, ethoxycarbonyl, propoxycarbonyl, 1-cyclopropylethoxycarbonyl, isopropoxycarbonyl, butoxycarbonyl, tertiarybutoxycarbonyl, pentyloxycarbonyl, hexyloxycarbonyl, etc.); lower alkanesulfonyl (e.g. mesyl, ethanesulfonyl, propanesulfonyl, isopropanesulfonyl, butanesulfonyl, etc.);

arenesulfonyl (e.g. benzenesulfonyl, tosyl, etc.); aroyl (e.g. benzoyl, toluoyl, xyloyl, naphthoyl, phthaloyl, indancarbonyl, etc.); ar(lower)alkanoyl (e.g. phenylacetyl, phenylpropionyl, etc.);

ar(lower)alkoxycarbonyl (e.g. benzyloxycarbonyl, phenethyloxycarbonyl, etc.), and the like. The acyl moiety as stated above may have at least one suitable substituent(s) such as halogen (chlorine, bromine, fluorine and iodine) or the like.

Suitable "$C_2$ to $C_6$ alkyl" for $R^2$ is one having 2 to 6 carbon atoms and may include ethyl, propyl, isopropyl, butyl, isobutyl, tert-butyl, pentyl, neopentyl, tert-pentyl, hexyl and the like.

The preferable examples of the object compound (I) are exemplified as follows.

Preferable example of $R^1$ is amino or lower alkanoyl amino; and $R^2$ is $C_2$ to $C_4$ alkyl.

The processes for preparing the object compounds of the present invention are explained in details in the following.

PROCESS 1

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide or the like; a derivative formed by reaction of the compound (II) with phosphorus trichloride or phosgene, and the like.

Suitable salt of the compounds (II) and (III) may include an acid addition salt such as an organic acid salt (e.g., acetate, maleate, tartrate, benzenesulfonate, toluenesulfonate, etc.) or an inorganic acid salt (e.g., hydrochloride, hydrobromide, sulfate, phosphate, etc.); a metal salt (e.g., sodium salt, potassium salt, calcium salt, magnesium salt, etc.); ammonium salt; an organic amine salt (e.g., triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride, an activated amide with imidazole, 4-substituted imidazole, dimethylpyrazole, triazole or tetrazole; or an activated ester (e.g., cyanomethyl ester, methoxymethyl ester, dimethyliminomethyl [$(CH_3)_2N^+=CH-$]ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester p-cresyl thioester, carboxymethyl thioester, pyranyl ester, pyridyl ester, piperidyl ester, 8-quinolyl thioester, etc.), or an ester with a N-hydroxy compound (e.g., N,N-dimethylhydroxylamine, 1-hydroxy-2-(1 H)-pyridone, N-hydroxysuccinimide, N-hydroxyphthalimide, 1-hydroxy-6-chloro-1 H-benzotriazole, etc.), and the like. These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (III) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methyl imidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride; phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1 H-benzotriazole; so-called Vilsmeier reagent prepared by the reaction of dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under copling or at ambient temperature.

In the present reaction, a syn isomer of the object compound (I) can be obtained preferably by conducting the present reaction of the compound (II) with the corresponding syn isomer of the starting compound (III), for example, in the presence of a Vilsmeier reagent as mentioned above etc. and under around neutral condition.

PROCESS 2

The object compound (Ib) or a salt thereof can be prepared by subjecting the compound (Ia) or a salt thereof to elimination reaction of the amino protective group.

Suitable salt of the compound (Ia) can be referred to those exemplified for the compound (II).

The elimination reaction is carried out in accordance with a conventional method such as hydrolysis; reduction; a method treating the compound (Ia) wherein $R^{1a}$ is acylamino with iminohalogenating agent, iminoetherifying agent and then, if necessary, hydrolyzing the resultant; or the like. The hydrolysis may include a method using an acid or base or hydrazine and the like. These methods may be selected depending on the kind of the protective groups to be eliminated.

Among these methods; hydrolysis using an acid is one of the most common and preferable method for eliminating the protective groups such as substituted or unsubstituted alkoxycarbonyl, for example, tert-pentyloxycarbonyl, lower alkanoyl (e.g., formyl, acetyl, etc.), cycloalkoxycarbonyl, substituted or unsubstituted aralkoxycarbonyl, aralkyl (e.g., trityl), substituted phenylthio, substituted aralkylidene, substituted alkylidene, substituted cycloalkylidene or the like. Suitable acid includes an organic or inorganic acid such as formic acid, trifluoroacetic acid, benenesulfonic acid, p-toluenesulfonic acid, hydrochloric acid and the like, and the most suitable acid is an acid which can easily be removed from the reaction mixture by a conventional manner such as distillation under reduced pressure, for example, formic acid, trifluoroacetic acid, hydrochloric acid, etc.

The acids can be selected according to the kind of the protective group to be eliminated. When the elimination reaction is conducted with an acid, it can be carried out in the presence or absence of a solvent. Suitable solvent includes water, a conventional organic solvent or a mixture thereof.

The elimination reaction using trifluoroacetic acid may be carried out in the presence of anisole. The hydrolysis using hydrazine is commonly applied for eliminating a phthaloyl, succinyl type aminoprotective group.

The hydrolysis using a base is preferably applied for elimination of an acyl group. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-ene, 1,4-diazabicyclo[2,2,2]octane, 1,5-diazabicyclo[5,4,0]undecene-5 or the like. The hydrolysis using a base is often carried out in water or a hydrophilic organic solvent or a mixed solvent thereof.

The reductive elimination is generally applied for eliminating the protective group, for example, haloalkoxycarbonyl (e.g. trichloroethoxycarbonyl, etc.), substituted or unsubstituted aralkoxy carbonyl (e.g. benzyloxycarbonyl, etc.), 2-pyridylmethoxycarbonyl, etc. Suitable reduction may include, for example, reduction with an alkali metal borohydride (e.g. sodium borohydride, etc.), reduction with a combination of a metal (e.g. tin, zinc, iron, etc.) or the said metal together with a metal salt compound (e.g. chromous chloride, chromous acetate, etc.) and an organic or inorganic acid (e.g. acetic acid, propionic acid, hydrochloric acid, etc.); and catalytic reduction. Suitable catalyst includes a conventional one, for example, Raney nickel, platinum oxide, palladium on charcoal and the like.

Among the protective groups, the acyl group can generally be eliminated by hydrolysis. Especially, halogen substituted-alkoxycarbonyl and 8-quinolyloxycarbonyl groups are usually eliminated by treating with a heavy metal such as copper, zinc, or the like.

Among the protective groups, the acyl group can also be eliminated by treating with an iminohalogenating agent (e.g. phosphorus oxychloride, etc.) and an iminoetherifying agent such as lower alkanol (e.g. methanol, ethanol, etc.), if necessary, followed by hydrolysis.

The reaction temperature is not critical and may suitable be selected in accordance with the kind of the protective group for the amino group and the elimination method as mentioned above, and the reaction is preferably carried out under a mild condition such as under cooling or at slightly elevated temperature.

The present invention includes, within its scope, the case that protected amino is transformed into the corresponding free amino according to the reaction conditions and kinds of the protective groups in the course of the aforementioned reactions and/or in post-treatment of the reactions in Processes 1 to 2.

In the aforementioned reactions and/or the post-treating of the reactions in Processes 1 to 2 of the present invention, the aforementioned geometrical isomer and/or tautomeric isomer may occasionally be transformed into the other geometrical isomer and/or tautomeric isomer and such cases are to be also included in the scope of the present invention.

In case that the object compound (I) has a free carboxy group and/or a free amino group, it may be transformed into its pharmaceutically acceptable salt as aforementioned by a conventional method.

The object compound (I) of the present invention exhibits high antimicrobial activity and inhibits the growth of a number of microorganisms including pathogenic Gram-positive and Gram-negative bacteria.

For therapeutic administration, the cephalosporin compounds according to the present invention are used in the form of pharmaceutical preparation which contain said compounds in admixture with a pharmaceutically acceptable carriers such as an organic or inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives.

While the dosage of the compounds may vary from and also depend upon the age and condition of the patient, an average single dose of about 50 mg., 100 mg., 250 mg., and 500 mg. of the compounds according to the present invention has proved to be effective for treating of infectious diseases caused by a number of pathogenic bacteria. In general amounts, daily dose between 1 mg/body and about 1000 mg/body or even more may be administered.

Now in order to show the utility of the object compounds (I), test data on anti-microbial activity of a representative compound of the present invention are shown below.

TEST METHOD

One loopful of an overnight culture of each test strain in Trypticase-soy broth ($10^8$ viable cells per ml.) was streaked on heart infusion agar (HI-agar) containing graded concentrations of antibiotics, and the minimal inhibitory concentration (MIC) was expressed in terms of $\mu$g/ml after incubation at 37° for 20 hours.

TEST COMPOUND

7-[2-Ethoxyimino-2-(2-aminothiazol-4-yl)acetamido]-3-(1-pyridiniomethyl)-3-cephem-4-carboxylate (syn isomer).

| Test Microorganism | Test results Test Compound |
|---|---|
| *Proteus Vulgaris* 1 | 0.050 |

EXAMPLE 1

2-Ethoxyimino-2-(2-formamidothiazol-4-yl)acetic acid (syn isomer) (2.2 g) was added to a solution of phosphorus pentachloride (2.0 g) in dichloromethane (40 ml) at −10° C., and stirred at −5° C. to −10° C. for 1 hour. After the addition of triethylamine (2.0 g), the resulting mixture was stirred at −5° C. for 5 minutes [Solution A]. N-trimethylsilylacetamide (9.8 g) was added to a stirred suspension of 1-[(7-amino-4-carboxy-3-cephem-3-yl)methyl]pyridinium chloride hydrochloride dihydrate (3.0 g) in dry tetrahydrofuran (60 ml), and the mixture was stirred for 20 minutes at 35° C. to 40° C. To the solution was added the solution A at −10° C. and the resulting solution was stirred at the same temperature for 40 minutes. Water and ethyl acetate were added to the reaction mixture at −10° C. and the separated aqueous layer was washed with ethyl acetate and adjusted to pH 4.0 with 10% aqueous solution of sodium hydroxide. The resulting solution was subjected to column chromatography on macroporous non-ionic adsorption resin "Diaion HP-20" (Trademark: Prepared by Mitsubishi Chemical Industries) and eluted with 10% aqueous solution of isopropyl alcohol. The fractions containing the object compound were collected and concentrated and lyophilized to give 7-[2-ethoxyimino-2-(2-formamidothiazol-4-yl)acetamido]-3-(1-pyridiniomethyl)-3-cephem-4-carboxylate (syn isomer) (1.52 g).

N.M.R. (DMSO-d6, $\delta$): 1.21 (3H, t, J=8.0 Hz), 3.10, 3.60 (2H, q, J=18.0 Hz), 4.10 (2 H, q, J=8.0 Hz), 5.12 (1H, d, J=4.0 Hz), 5.17, 5.71 (2H, q, J=14.0 Hz), 5.70 (1H, dd, J=4.0 and 8.0 Hz), 7.33 (1H, s), 8.13 (2H, dd, J=6.0 Hz), 8.52 (1H, s), 8.53 (1H, d, J=6.0 Hz), 9.45 (2H, d, J=6.0 Hz), 9.57 (1H, d, J=8.0 Hz)

EXAMPLE 2

Phosphorus oxychloride (1.7 g) was added to a stirred suspension of 2-propoxyimino-2-(2-aminothiazol-4-yl)acetic acid (syn isomer) (2.0 g) in dry tetrahydrofuran (20 ml) and water (0.114 g) at 0° to 3° C. and the resulting mixture was stirred for 30 minutes and thereto was added N-trimethylsilylacetamide (1.2 g) at the same temperature. The resulting mixture was stirred for 15 minutes and thereto was added phosphorus oxychloride (1.7 g) at the same temperature and then stirred for 15 minutes. To the resulting mixture was added dry N,N-dimethylformamide (0.9 g) at the same temperature and then stirred for 30 minutes [Solution A]. N-trimethylsilylacetamide (11.4 g) was added to a stirred suspension of 1-[(7-amino-4-carboxy-3-cephem-3-yl)methyl]pyridinium chloride hydrochloride dihydrate (3.5 g) in tetrahydrofuran (70 ml). To the resulting solution was dropwise added the Solution A at −5° C. and stirred at 0° to −5° C. for 40 minutes. To the reaction mixture was added water and ethyl acetate at −5° C. The aqueous layer was separated, washed with ethyl acetate and then adjusted to pH 4.0 with 10% aqueous solution of sodium hydroxide under ice-cooling. The solution was subjected to column chromatography on macroporous non-ionic adsorption resin "Diaion HP-20" (Trademark: Prepared by Mitsubishi Chemical Industries) and eluted with 20% aqueous solution of isopropyl alcohol. The fractions containing the object compound were collected, concentrated and lyophilized to give 7-[2-propoxyimino-2-(2-aminothiazol-4-yl)acetamido]-3-(1-pyridiniomethyl)-3-cephem-4-carboxylate (syn isomer).

I.R. (Nujol): 3300, 3170, 1750, 1610 cm$^{-1}$.

N.M.R. (D2O, $\delta$): 0.90 (3H, t, J=7.0 Hz), 1.37-2.10 (2H, m), 3.18, 3.72 (2H, q, J=18.0 Hz), 4.17 (2H, t, J=7.0 Hz), 5.29 (1H, d, J=5.0 Hz), 5.35, 5.66 (2H, q, J=14.0 Hz), 5.87 (1H, d, J=5.0 Hz), 6.91 (1H, s), 8.09 (2H, dd, J=6.0 Hz), 8.60 (1 H, m), 8.98 (2H, d, J=6.0 Hz).

EXAMPLE 3

The following compounds were prepared according to the similar manners to those of Examples 1 and 2.
(1) 7-[2-Ethoxyimino-2-(2-aminothiazol-4-yl)acetamido]-3-(1-pyridiniomethyl)-3-cephem-4-carboxylate (syn isomer).
I.R. (Nujol): 3130, 1780, 1670, 1610 cm$^{-1}$.
(2) 7-[2-Isopropoxyimino-2-(2-formamidothiazol-4-yl)-acetamido]-3-(1-pyridiniomethyl)-3-cephem-4-carboxylate (syn isomer).
N.M.R. (DMSO-d6, $\delta$): 1.21 (6H, d, J=6.0 Hz), 3.07, 3.56 (2H, q, J=17.0 Hz), 4.32 (1H, m), 5.09 (1H, d, J=5.0 Hz), 5.21, 5.68 (2H, q, J=14.0 Hz), 5.68 (1H, dd, J=5 and 8 Hz), 7.30 (1H, s), 8.11 (2H, dd, J=6.0 Hz), 8.48 (1H, s), 8.50 (1H, m), 9.27-9.56 (3H, m).
(3) 7-[2-Isopropoxyimino-2-(2-aminothiazol-4-yl)-acetamido]-3-(1-pyridiniomethyl)-3-cephem-4-carboxylate (syn isomer).
I.R. (Nujol): 3350, 1780, 1670, 1610 cm$^{-1}$.

EXAMPLE 4

A mixture of 7-[2-ethoxyimino-2-(2-formamidothiazol-4-yl)acetamido]-3-(1-pyridiniomethyl)-3-cephem-4-carboxylate (syn isomer) (1.4 g) in methanol (20 ml) and conc. hydrochloric acid (0.85 g) were stirred for 2.5 hours at room temperature. The reaction mixture was added to a mixture of water and ethyl acetate. The aqueous layer was separated, washed with ethyl acetate and adjusted to pH 4.0 with 10% aqueous solution of sodium hydroxide. The resulting solution was subjected to column chromatography on macroporous non-ionic adsorption resin "Diaion HP-20" (Trademark: prepared by Mitsubishi Chemical Industries) and eluted with 5% aqueous solution of isopropyl alcohol. The fractions containing the object compound were concentrated and lyophilized to give 7-[2-ethoxyimino-2-(2-aminothiazol-4-yl)acetamido]-3-(1-pyridiniomethyl)-3-cephem-4-carboxylate (syn isomer) (0.35 g).

I.R. (Nujol): 3130, 1780, 1670, 1610 cm$^{-1}$.

N.M.R. (DMSO-d6, $\delta$): 1.28 (3H, t, J=7.0 Hz), 3.12-3.87 (2H, m), 4.07 (2H, q, J=7.0 Hz), 5.09 (1H, d, J=5.0 Hz), 5.46, 5.71 (2H, q, J=14.0 Hz), 5.69 (1H, dd, J=5.0 and 8.0 Hz), 6.69 (1H, s), 7.18 (2H, broad s), 8.16 (2H, dd, J=6.0 Hz), 8.53 (1H, d, J=6.0 Hz), 9.31-9.66 (3H, m).

EXAMPLE 5

The following compounds were prepared according to the similar manner to that of Example 4.
(1) 7-[2-Propoxyimino-2-(2-aminothiazol-4-yl)acetamido]-3-(1-pyridiniomethyl)-3-cephem-4-carboxylate (syn isomer)
I.R. (Nujol): 3300, 3170, 1750, 1610 cm$^{-1}$.
(2) 7-[2-Isopropoxyimino-2-(2-aminothiazol-4-yl)acetamido]-3-(1-pyridiniomethyl)-3-cephem-4-carboxylate (syn isomer).
I.R. (Nujol): 3350, 1780, 1670, 1610 cm$^{-1}$.
N.M.R. (DMSO-d6, $\delta$): 1.99 (6H, d, J=7.0 Hz), 3.11-3.81 (2H, m), 4.26 (1H, m), 5.08 (1H, d, J=5.0 Hz), 5.16, 5.68 (2H, q, J=14.0 Hz), 5.67 (1H, dd, J=5.0 and 8.0 Hz), 6.65 (1H, s), 7.16 (2H, broad s), 8.13 (1H, m), 9.25–9.58 (3H, m).

What we claim is:
1. 7-[2-ethoxyimino-2-(2-aminothiazol-4-yl)acetamido]-3-(1-pyridiniomethyl)-3-cephem-4-carboxylate (syn isomer).
2. A pharmaceutical composition comprising an effective amount of the compound of claim 1 or pharmaceutically acceptable salt thereof in association with a pharmaceutically acceptable, substantially non-toxic carrier or excipient.

* * * * *